United States Patent
Greenhalgh et al.

(10) Patent No.: US 8,945,137 B1
(45) Date of Patent: Feb. 3, 2015

(54) BONE GRAFT DELIVERY SYSTEM AND METHOD FOR USING SAME

(71) Applicant: Sierra Surgical LLC, Delray Beach, FL (US)

(72) Inventors: Travis Greenhalgh, Boca Raton, FL (US); Ryan Lewis, Waxhaw, NC (US)

(73) Assignee: Surgical Device Exchange, LLC, Boca Raton, FL (US)

( * ) Notice: Subject to any disclaimer, the term of this patent is extended or adjusted under 35 U.S.C. 154(b) by 0 days.

(21) Appl. No.: 14/162,102

(22) Filed: Jan. 23, 2014

Related U.S. Application Data

(60) Provisional application No. 61/798,513, filed on Mar. 15, 2013.

(51) Int. Cl.
| | | |
|---|---|---|
| A61B 17/58 | (2006.01) | |
| A61B 17/60 | (2006.01) | |
| A61F 2/00 | (2006.01) | |
| A61B 17/88 | (2006.01) | |

(52) U.S. Cl.
CPC .................................. *A61B 17/8805* (2013.01)
USPC .............................................. 606/99; 606/93

(58) Field of Classification Search
USPC ................................. 606/93, 94, 99
See application file for complete search history.

(56) References Cited

U.S. PATENT DOCUMENTS

| | | | | |
|---|---|---|---|---|
| 2,316,095 | A * | 4/1943 | Mead, Jr. ..................... | 604/209 |
| 4,277,184 | A * | 7/1981 | Solomon ..................... | 366/139 |
| 4,338,925 | A | 7/1982 | Miller | |
| 6,439,439 | B1 * | 8/2002 | Rickard et al. ............... | 222/391 |
| 6,814,736 | B2 | 11/2004 | Reiley et al. | |
| 7,141,054 | B2 | 11/2006 | Vandewalle | |
| 7,306,603 | B2 | 12/2007 | Boehm, Jr. et al. | |
| 7,513,901 | B2 | 4/2009 | Scifert et al. | |
| 7,799,033 | B2 | 9/2010 | Assell et al. | |
| 7,811,291 | B2 | 10/2010 | Liu et al. | |
| 7,887,543 | B2 | 2/2011 | Sand et al. | |
| 2004/0024409 | A1 | 2/2004 | Sand et al. | |
| 2004/0133211 | A1 | 7/2004 | Raskin et al. | |
| 2005/0137604 | A1 | 6/2005 | Assell et al. | |
| 2005/0171549 | A1 | 8/2005 | Boehm, Jr. et al. | |
| 2005/0203523 | A1 | 9/2005 | Wenstrom, Jr. et al. | |
| 2006/0293687 | A1 | 12/2006 | Bogert | |
| 2007/0005072 | A1 | 1/2007 | Castillo et al. | |
| 2007/0276397 | A1 | 11/2007 | Pacheco | |
| 2008/0065082 | A1 | 3/2008 | Chang et al. | |
| 2008/0125856 | A1 | 5/2008 | Perez-Cruet et al. | |
| 2008/0300684 | A1 | 12/2008 | Shelokov | |
| 2009/0216238 | A1 | 8/2009 | Stark | |
| 2009/0318925 | A1 | 12/2009 | Campion et al. | |
| 2010/0057087 | A1 | 3/2010 | Cha | |
| 2010/0174286 | A1 | 7/2010 | Truckai et al. | |
| 2010/0179556 | A1 | 7/2010 | Scribner | |
| 2010/0204702 | A1 | 8/2010 | Lechot et al. | |
| 2010/0262146 | A1 | 10/2010 | Tulkis | |
| 2011/0071527 | A1 | 3/2011 | Nelson et al. | |
| 2011/0071536 | A1 | 3/2011 | Kleiner et al. | |
| 2012/0253316 | A1 | 10/2012 | Oktavec et al. | |

* cited by examiner

*Primary Examiner* — Andrew Yang
(74) *Attorney, Agent, or Firm* — Knobbe, Martens, Olson & Bear, LLP.

(57) ABSTRACT

A bone graft delivery system can include an elongate tube, a handle having a trigger, and a tip. The trigger is actuated to deliver bone graft material through the tube. The tip has one or more openings to deliver the bone graft material to a desired location and includes a surface suitable to act as a rasp for decorticating bone. A method for delivering bone graft material to a desired surgical location includes providing a bone graft delivery device, positioning the device adjacent the surgical location, decorticating bone, and delivering bone graft material to the surgical location.

17 Claims, 17 Drawing Sheets

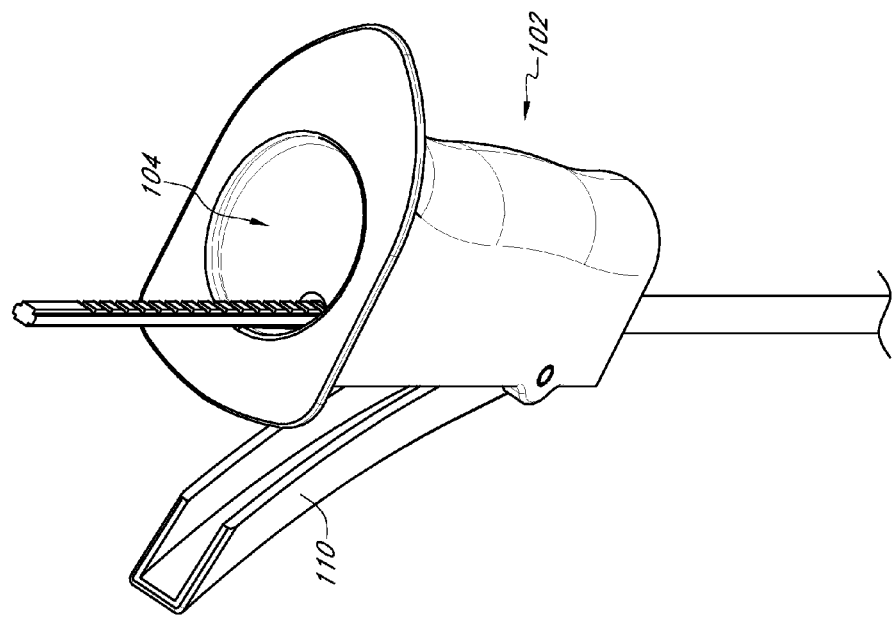

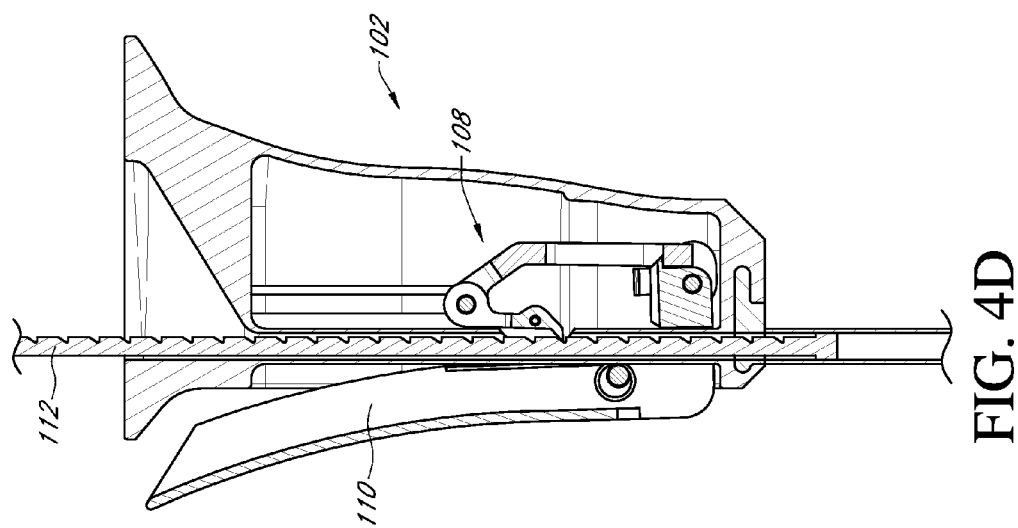

BONE GRAFT DELIVERY SYSTEM AND METHOD FOR USING SAME

CROSS-REFERENCE TO RELATED APPLICATIONS

This application claims priority benefit of U.S. Provisional Application No. 61/798,513, filed Mar. 15, 2013, the entirety of which is hereby incorporated by reference herein and should be considered a part of this specification.

BACKGROUND

1. Field

The present application relates to orthopedic surgery in general, and more particularly, to bone graft delivery systems and methods.

2. Description of the Related Art

In a bone grafting procedure, a surgeon places bone or a bone substitute into an area in a patient's body to provide a type of scaffold for bone growth and repair. Bone grafts can be used to help treat various orthopedic problems, for example, to fuse a joint or repair a fracture. Bone graft material can be, for example, autogenous (harvested from the patient's own body), allogeneic (harvested from another person, usually a cadaver), or synthetic. Many bone grafting procedures are performed via open surgery implantation. However, these procedures can be performed minimally invasively, for example, by using a needle to inject the bone graft material into the target location without requiring a surgical incision.

In some cases decortication of the bony area receiving the graft is performed prior to delivery of the bone graft material. Decortication removes superficial cortical bone and exposes the underlying cancellous bone, which can help accelerate the integration of the bone graft with the native bone.

SUMMARY

The devices, systems, and methods described herein allow for minimally invasive delivery of bone graft material to a desired location in a patient's body. In some embodiments, the devices, systems, and methods described herein also provide for bone decortication.

In some embodiments, a bone graft delivery system includes an elongate tube, a handle at a proximal end of the tube configured to be actuated to deliver bone graft material through the tube, and a tip at a distal end of the tube. The handle may include a trigger. The tip includes one or more openings configured to deliver the bone graft material to a desired location and a surface suitable to serve as a rasp for scraping bone.

In some embodiments, a method for delivering bone graft material to a surgical location includes providing a bone graft delivery device comprising an elongate tube and a distal tip having at least one opening for delivering the bone graft material to the surgical location and positioning the device adjacent the surgical location. The method further includes decorticating bone with the distal tip and delivering bone graft material through the tube and out the at least one opening of the tip.

BRIEF DESCRIPTION OF THE DRAWINGS

FIG. 3 illustrates a perspective view of a handle of the bone graft delivery device of FIG. 1;

FIGS. 4A-4E are section views illustrating operation of a ratcheting mechanism in the handle of FIG. 3;

DETAILED DESCRIPTION

Figure 1:
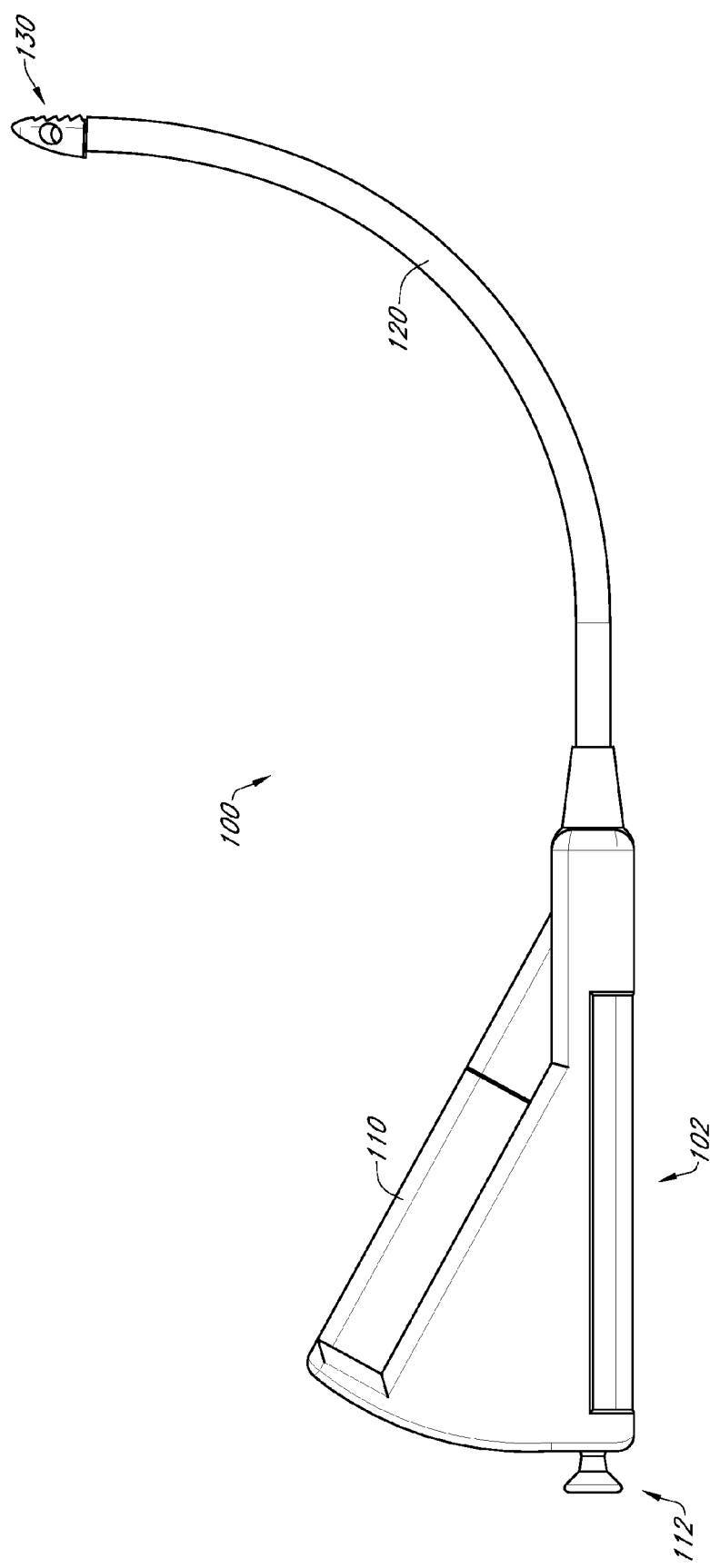
FIG. 1 illustrates a side view of an example embodiment of a bone graft delivery device.
Figure 2:
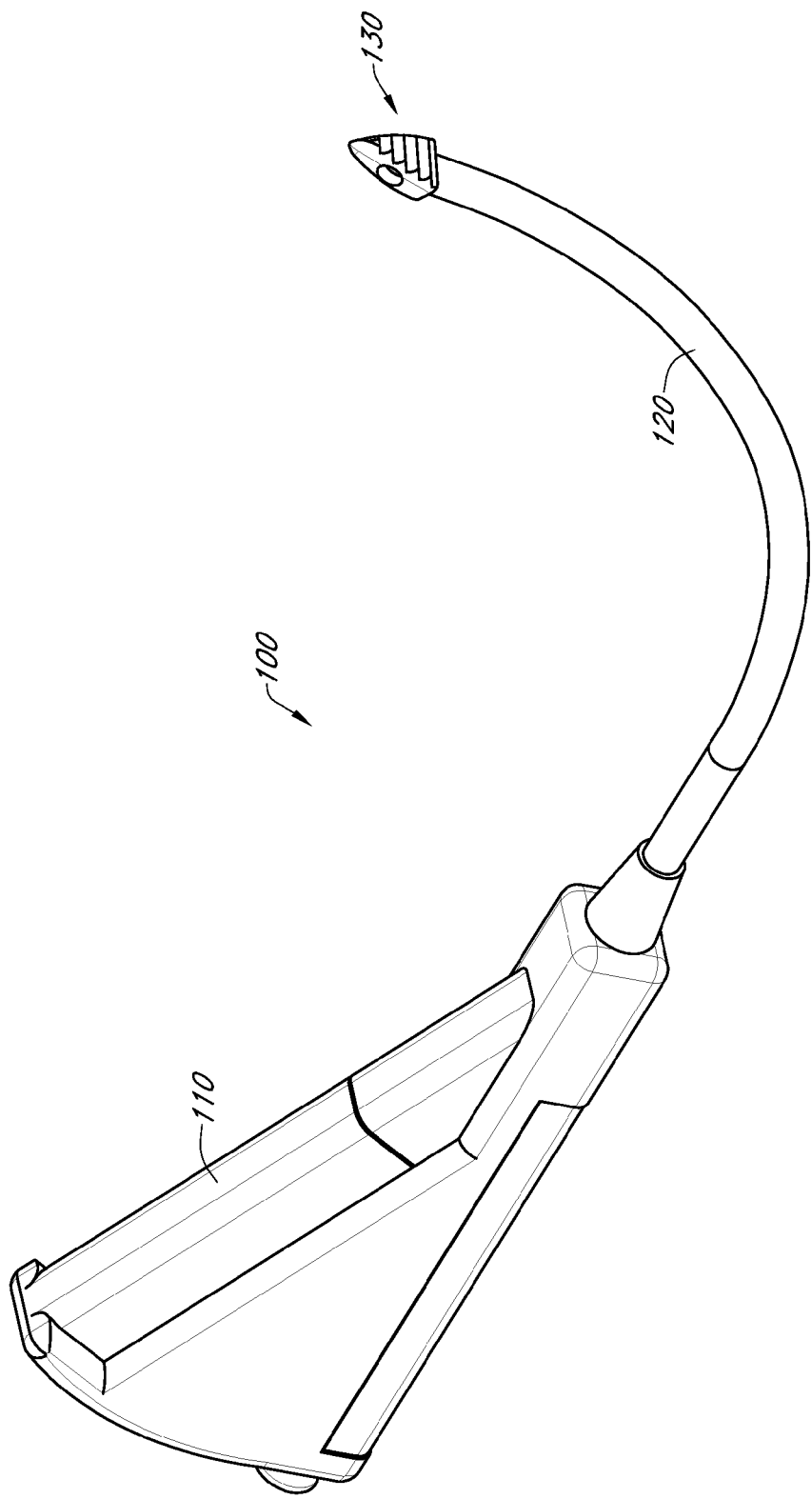
FIG. 2 illustrates a perspective view of the bone graft delivery device of FIG. 1.

As shown in FIGS. 1 and 2, a bone graft delivery device 100 generally includes a handle 102 having a trigger 110 or other actuation mechanism, a tube 120 having a lumen therethrough, and a distal tip 130. In the illustrated embodiment, the bone graft delivery device 100 is similar to a caulking gun. The handle 102 can house a supply of the desired bone graft material. The bone graft material can be pre-loaded in the handle 102 or can be supplied to the handle via a cartridge that can be removably coupled to the handle 102. In some embodiments, the device 100 can further include a plunger 112 that is retracted proximally to allow the handle to receive a cartridge or pre-loaded volume of bone graft material.

In use, the trigger 110 is actuated to deliver bone graft material through the tube 120 and distal tip 130 to a desired surgical location. In some embodiments, the plunger 112 is simultaneously pushed distally to help deliver bone graft material through the tube 120. In some embodiments, the trigger 110 or other actuation mechanism is configured to deliver a controlled release amount of bone graft material during actuation of the device, for example, ½ cc of bone graft material per complete squeeze of the trigger 110. The trigger 110 or other actuation mechanism may be operated manually or by mechanical, battery powered, electric, pneumatic, or any other means of force.

In some embodiments, a base of the handle 102 can include a funnel 104 configured to receive the bone graft material, as shown in FIG. 3. Whereas some existing bone graft delivery devices are only compatible with certain, e.g., pre-packaged, bone graft materials, the funnel 104 can be designed to advantageously allow the user to use any bone graft material or combination of bone graft materials he or she wishes or deems appropriate. For example, the user can use synthetic, autologous, stem cell, DMB, cadaveric, and/or any other available bone graft material. The handle 102 can further include a channel 106 extending therethrough connecting and in fluid communication with the funnel 104 and tube 120. The user can mix the desired bone graft material in the funnel 104, then use the plunger 112 or other means to advance the bone graft material through the channel 106 and into the tube 120 for delivery.

Figure 4A:
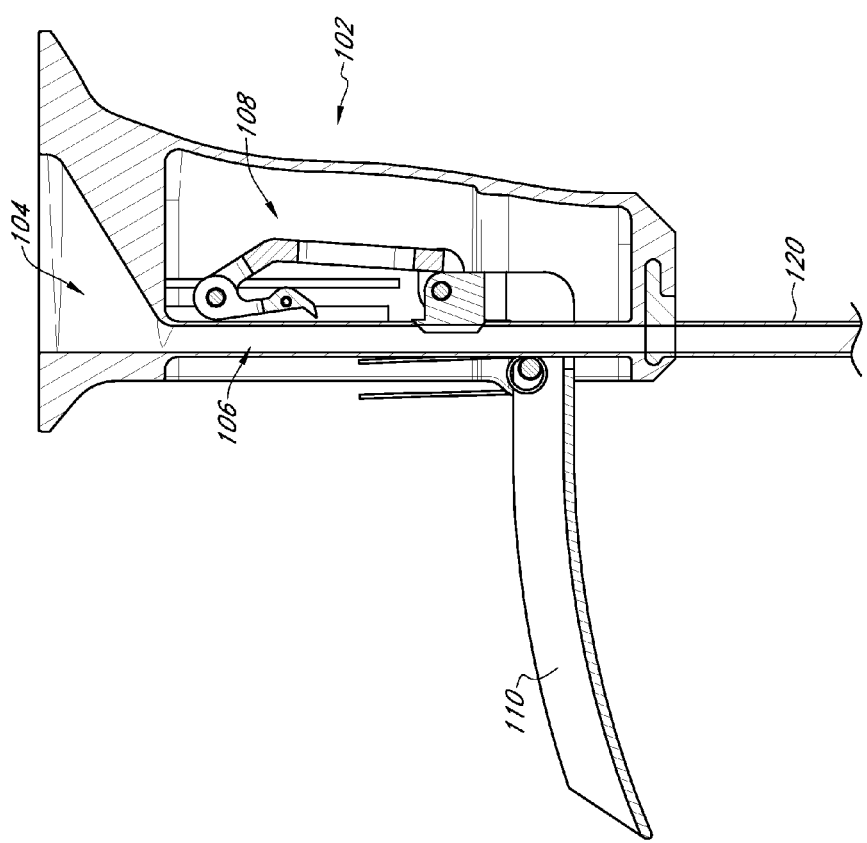
Figure 4B:
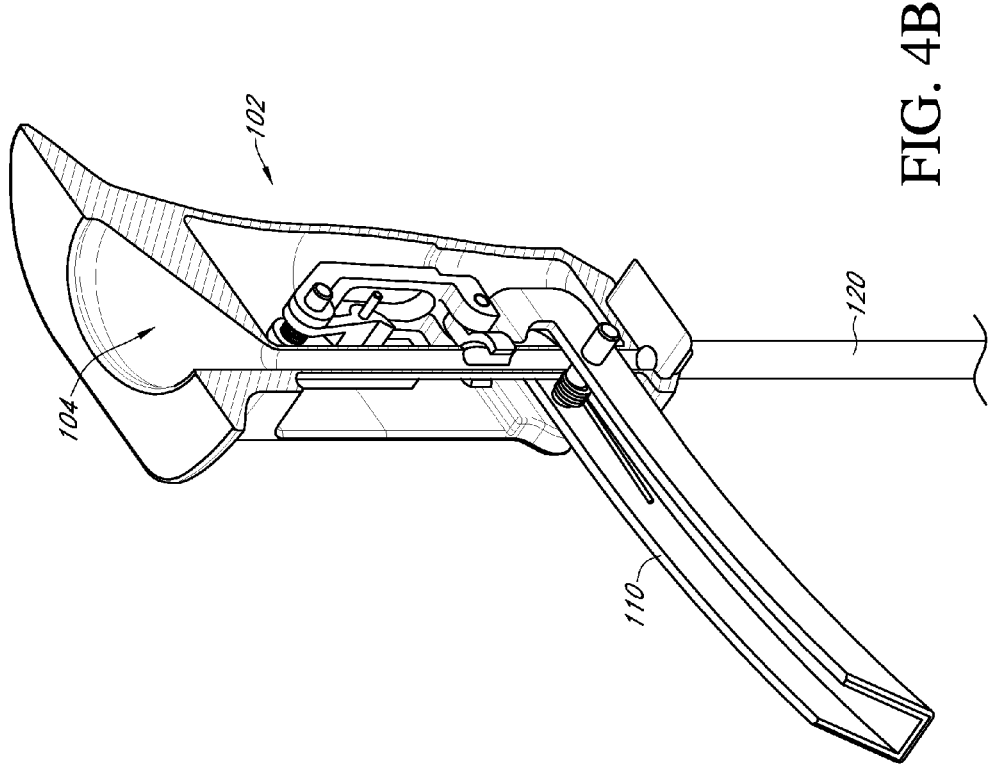
Figure 4C:
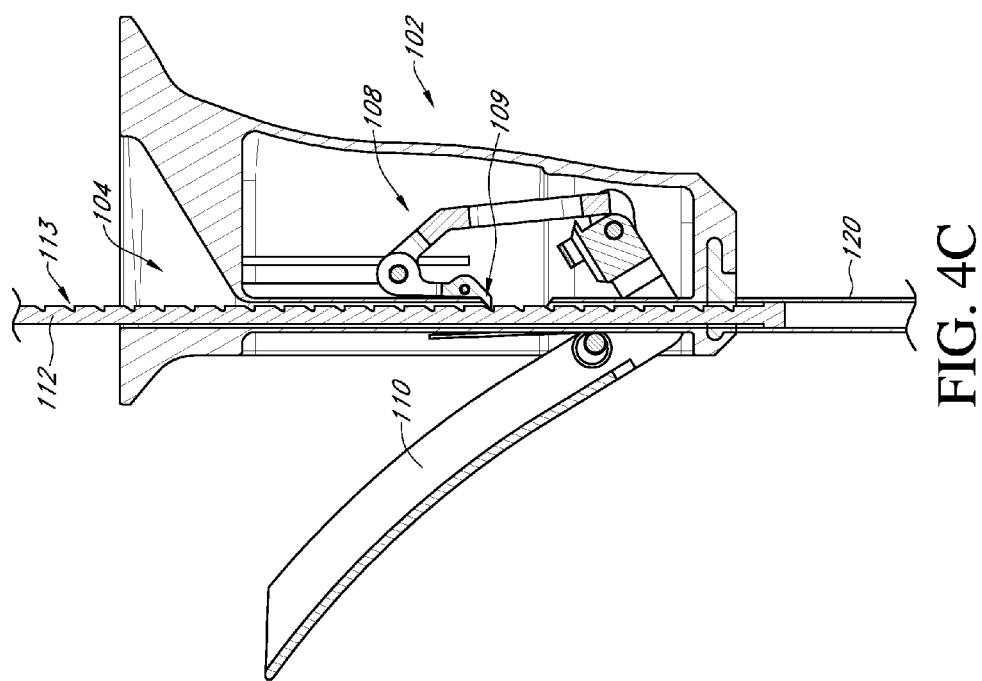
Figure 4E:
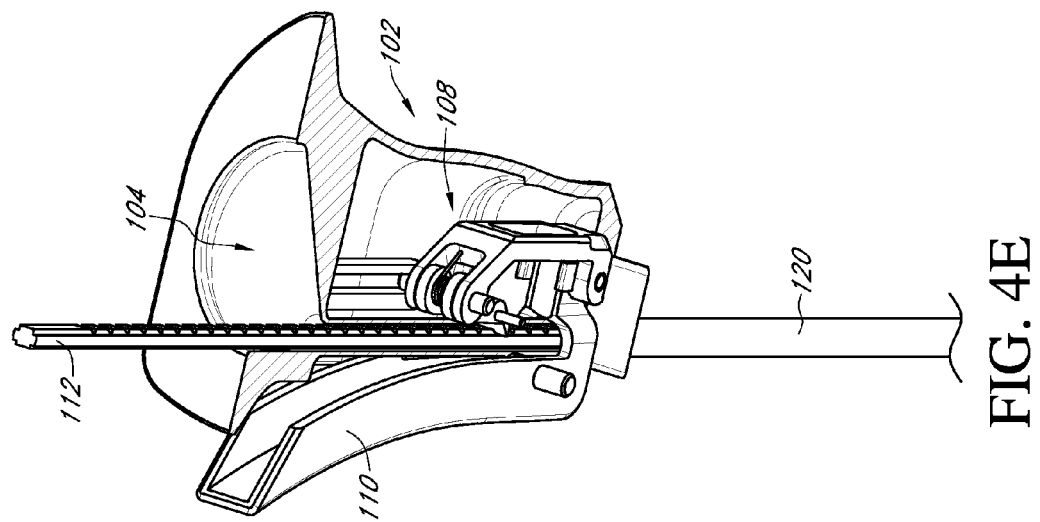

In some embodiments, the handle 102 includes a ratcheting mechanism 108 configured to advance bone graft material from the funnel 104 and channel 106 through the tube 120 for delivery. As illustrated in FIGS. 4A and 4B, extending the trigger 110 away from the handle 102, for example to a position perpendicular to the handle 102, can place the ratcheting mechanism 108 in a closed position that does not allow interior access for the plunger 112 to allow for loading of the bone graft material through the funnel 104 into the channel 106. Once the bone graft material has been loaded, the trigger 110 can be moved toward the handle 102 to an intermediate position, as shown in FIG. 4C, to open the channel 106 and allow the plunger 112 to be inserted into the channel 106. An arm 109 of the ratcheting mechanism 108 engages one of a series of notches 113 on the plunger 112. Movement of the trigger 110 to a final position closest the handle 102 causes the arm 109 of the ratcheting mechanism 108 to move distally within the handle 102 (or away from the funnel 104 and toward the tube 120), thereby advancing the plunger 112 distally within the channel 106 to force the bone graft material distally within the channel 106 and/or tube 120, as shown in FIGS. 4D and 4E. The trigger 110 can be moved back to the intermediate position to cause the ratcheting mechanism 108 to move proximally within the handle 102 (or toward the funnel 104) and the arm 109 to slide proximally along the plunger 112 to engage a more proximal notch 112. The trigger 110 can be moved between the intermediate position and final position multiple times until the arm 109 has reached the proximal end of the plunger 112.

Figure 6A:
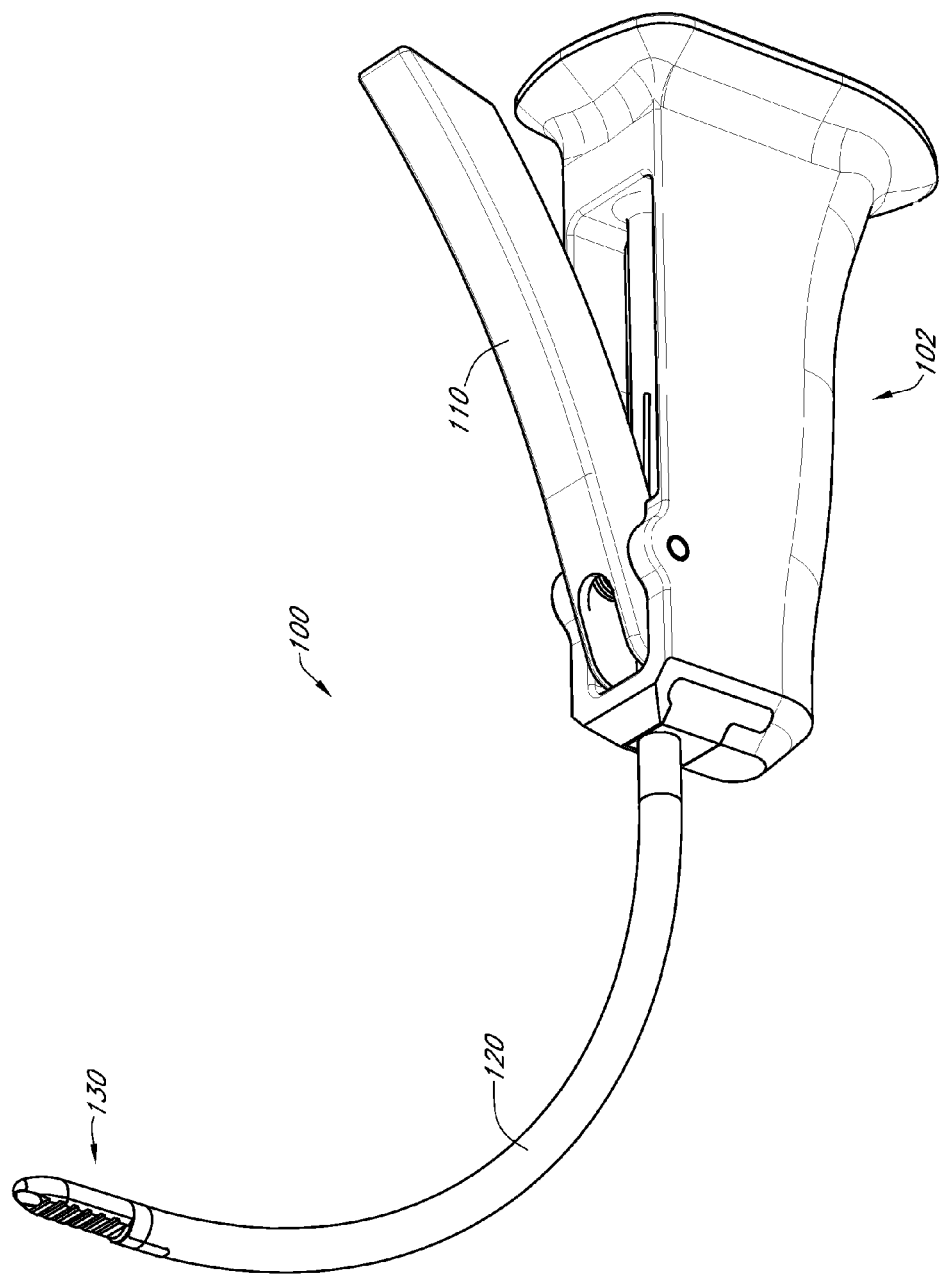
FIG. 6A illustrates a perspective view of an example embodiment of a bone graft delivery device.
Figure 6B:
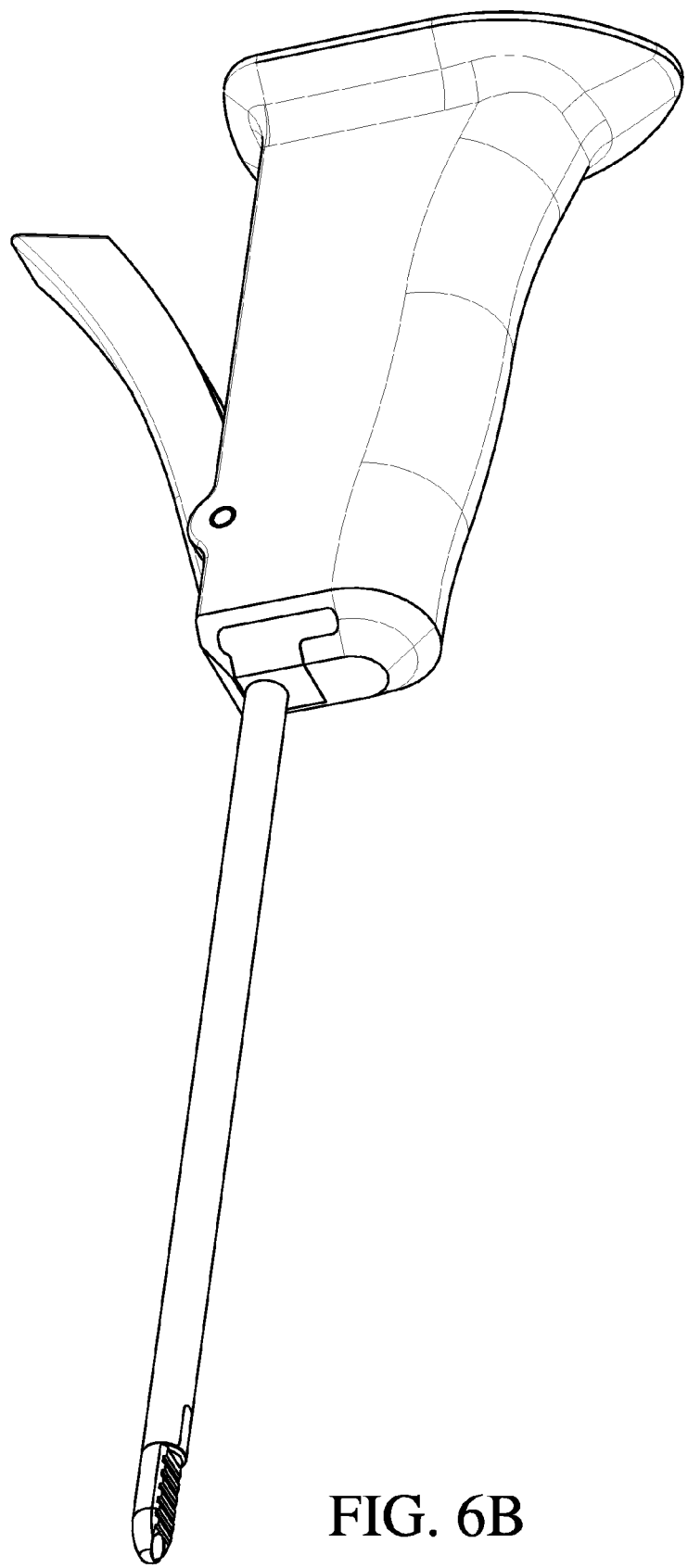
FIG. 6B illustrates a perspective view of an example embodiment of a bone graft delivery device.
Figure 6C:
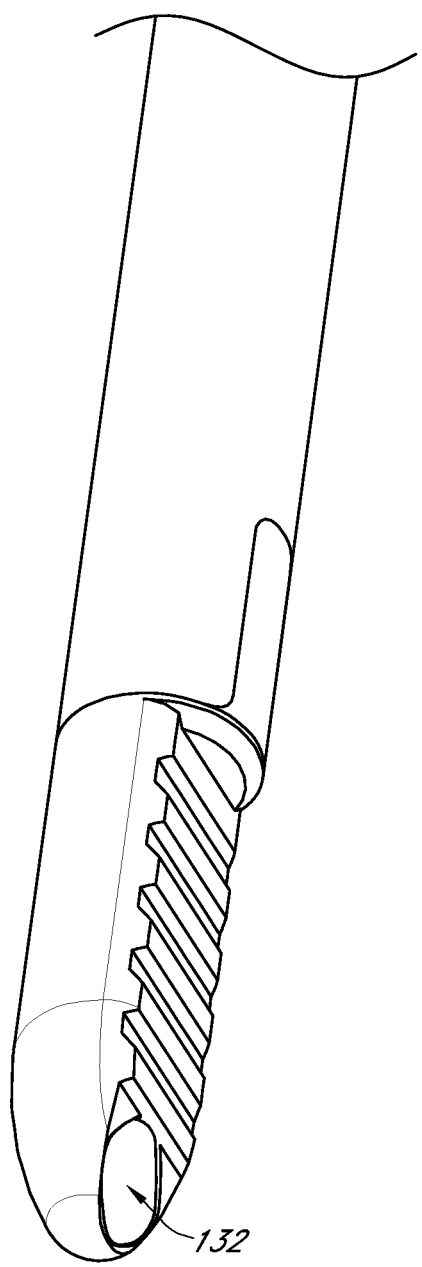
FIG. 6C illustrates an enlarged view of a distal tip of the bone graft delivery device of FIG. 6B.

As shown in FIGS. 1 and 2, the tube 120 can include a permanent bend or curve that may be useful in positioning the device 100 at a desired location, for example, a space between two spinal discs. Alternatively, the tube 120 may be straight, for example, as shown in FIG. 6B, to deliver bone graft material directly into a desired location such as a disc space. In some embodiments, the tube 120 is somewhat flexible or repositionable and can be manipulated to bend or curve the tube 120 as needed to reach the desired location. In some embodiments, the tube 120 is made of a rigid material, for example, a plastic, composite, or metal, and is generally hollow to allow for the passage of bone graft material through the tube 120.

Figure 5A:
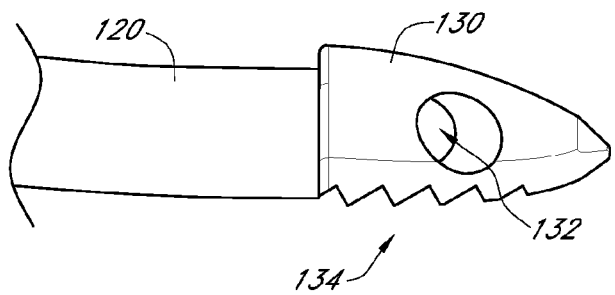
FIGS. 5A-5C illustrate various views of a distal tip of the bone graft delivery device of FIGS. 1 and 2.
Figure 5B:
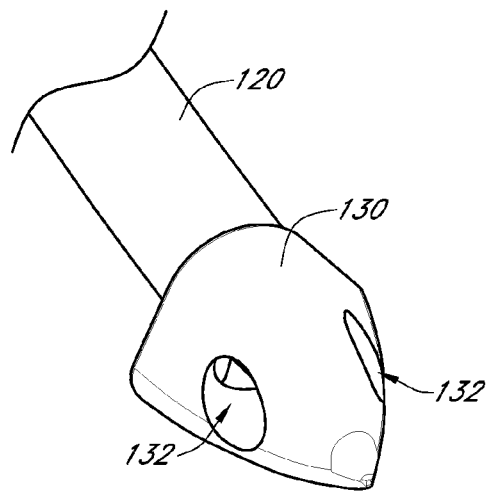
Figure 5C:
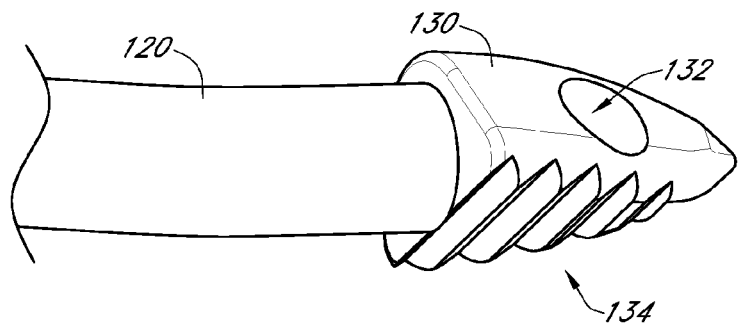
Figure 6D:
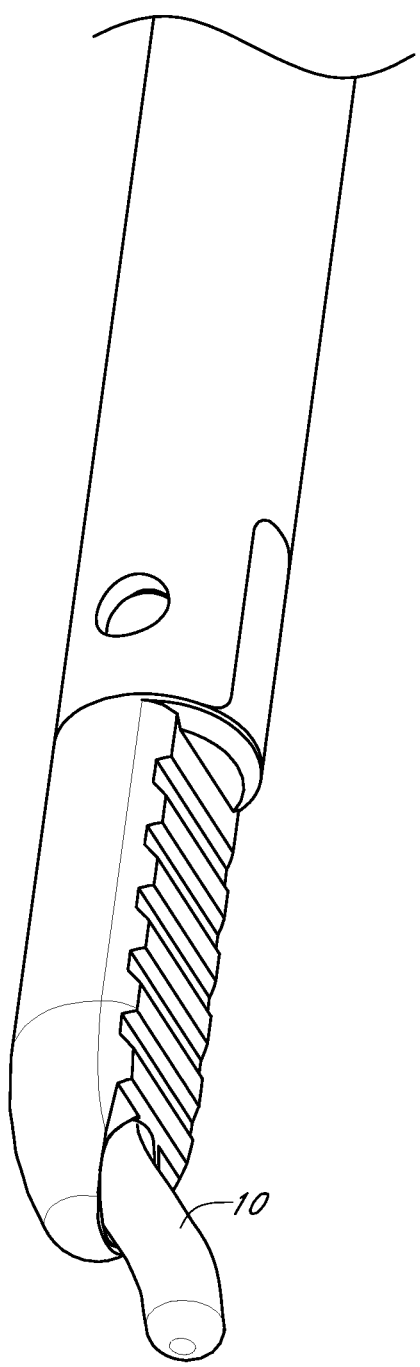
FIG. 6D illustrates the distal tip of FIG. 6C extruding bone graft material.

As shown in FIGS. 5A-5C, a distal end of the tube 120 includes a tip 130. The tip 130 can be integrally formed with or coupled, removably or permanently, to the tube 120. In the illustrated embodiment, the tip 130 is somewhat bullet-shaped with a generally triangular cross-section; however, other shapes and configurations are also possible. For example, the tip 130 can be generally flat as shown in the example embodiments of FIGS. 6A-6D. In some embodiments, the tip 130 is pointed and/or sharp to dissect or split muscle and tissue as it is advanced through the patient's skin and body to the surgical location. Alternatively, the tip 130 can be blunt to allow for displacement of muscle without risk of cutting of nerves or other tissue. The tip has a single or multiple openings 132 in fluid communication with the tube 120 lumen and configured to deliver the bone graft material 10 from the tube 120, as shown in FIG. 6D, to the desired location.

In some embodiments, at least one side or area of the tip 130 includes a series of jagged edges or other suitable surface 134 configured to serve as a rasp for scraping bone. The rasp may be operated manually or by mechanical, battery powered, electric, pneumatic, or any other means of force to allow for decortication of the area to receive the bone graft material.

In some embodiments, the delivery device 100 includes a sleeve slidably or telescopingly disposed over the tip 130. In some embodiments, the sleeve can extend to a proximal end of the tube 120 adjacent the handle 102 so that a user can distally advance or proximally retract the sleeve by manipulating a proximal end of the sleeve. In other embodiments, the sleeve extends over only a portion of the tube 120 or over only the tip 130 and the delivery device 100 includes an actuating mechanism that allows the sleeve to be advanced and retracted. The sleeve can be disposed over the tip 130 during insertion of the tip 130 to the target area to advantageously protect skin, tissue, and/or muscle along the insertion path from damage or injury from the rasping surface 134 and to allow the tip 130 to pass through the skin, tissue, and/or muscle more easily. Once the tip is positioned in the target location, the sleeve can be proximally retracted to expose the rasping surface 134 for decortication of the target area. After decortication and/or after delivery of the bone graft material, the sleeve can be distally advanced to cover the rasping surface 134 for withdrawal of the tip 130 from the body.

Figure 7A:
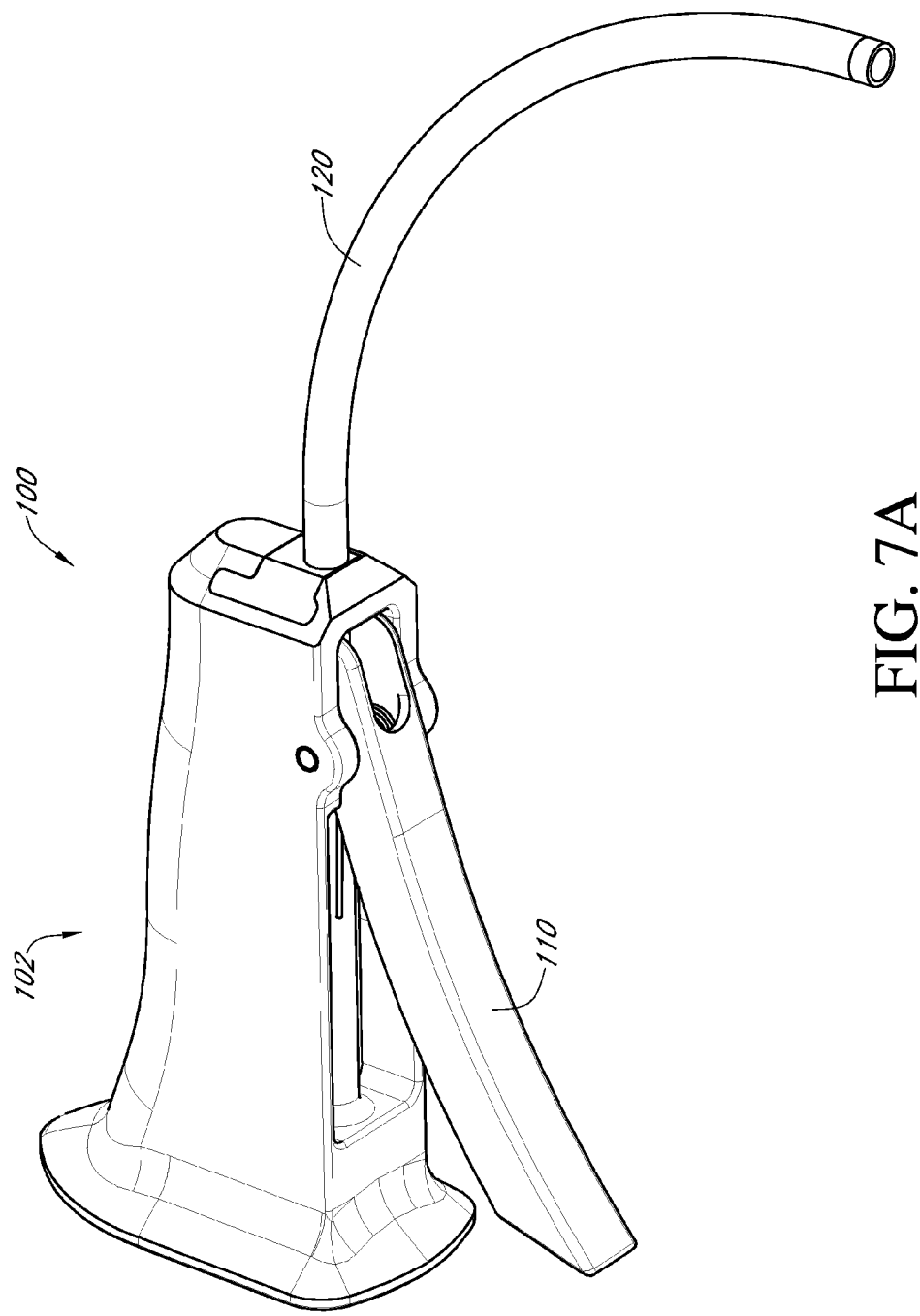
FIG. 7A illustrates a perspective view of an example embodiment of a bone graft delivery device.
Figure 7B:
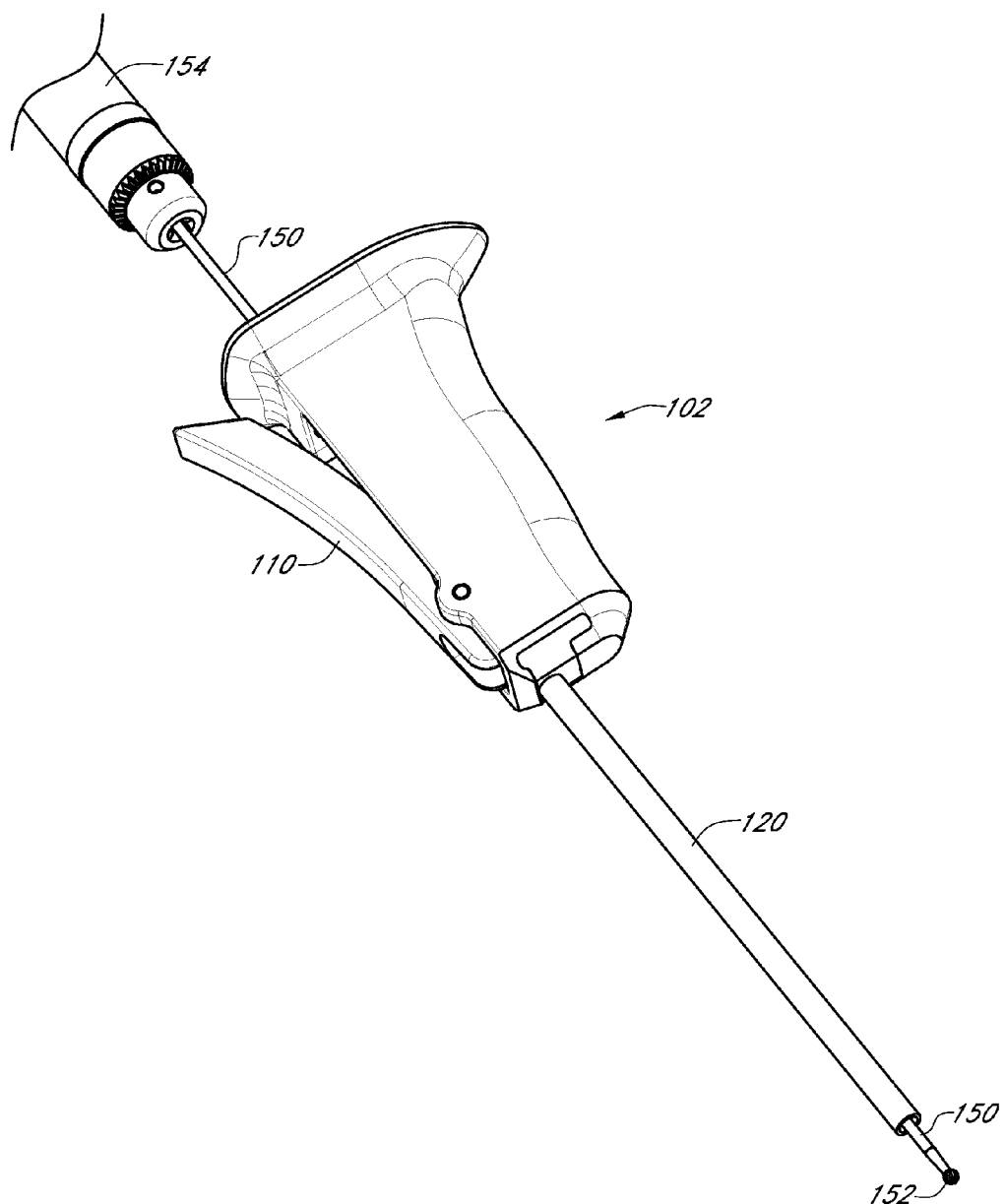
FIG. 7B illustrate the bone graft delivery device of FIG. 7A including a shaft having a distal burr disposed therethrough.
Figure 7C:
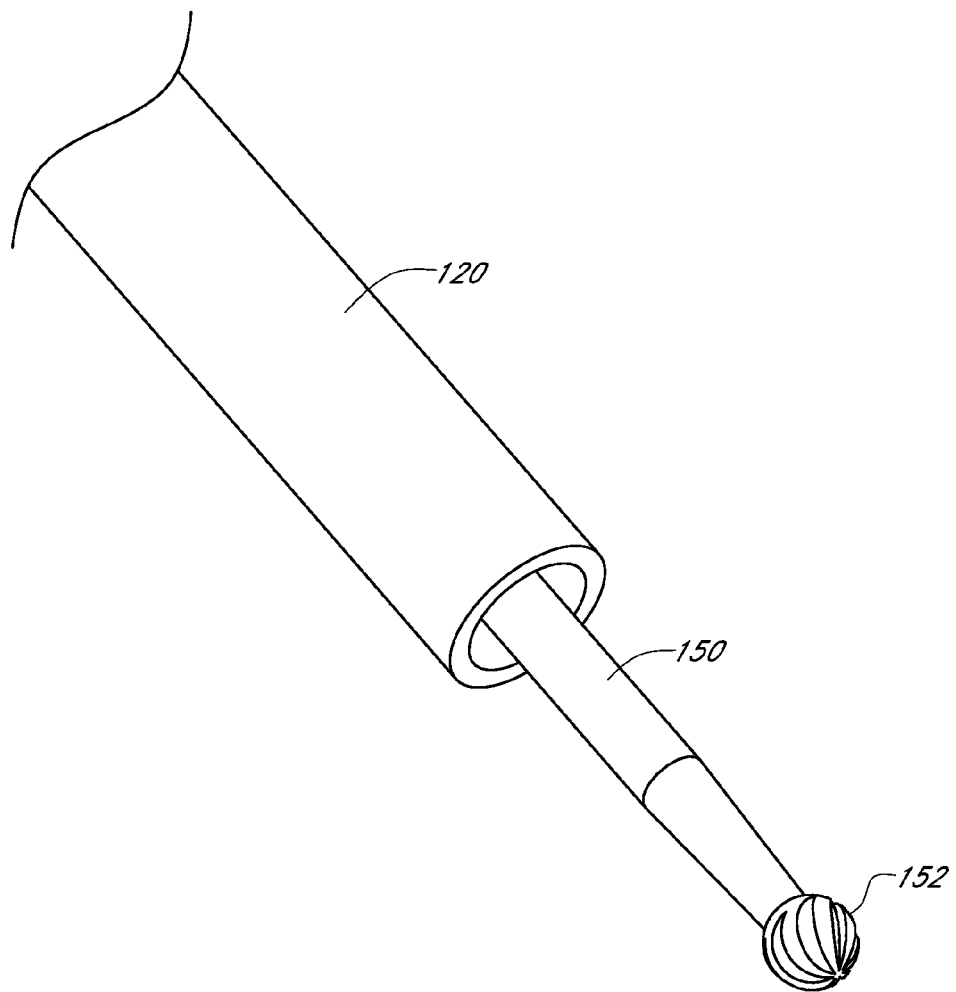
FIG. 7C illustrates an enlarged view of the distal end of the bone graft delivery device of FIG. 7B.

In some embodiments, the distal end of the tube 120 does not include a rasping tip 130 as shown in FIG. 7A. Instead, an elongate shaft 150 having a burr 152 at a distal end can be inserted through the tube 120 as needed or desired to decorticate a target area, for example as shown in FIGS. 7B and 7C. The use of a separate instrument for decortication can advantageously allow the user to select different burrs, rasps, or the like for different patients, target areas, or situations. The elongate shaft 150 and burr 152 can be operated manually. Alternatively, a proximal end of the shaft 150 can be coupled to a drill 154 or another device to provide decortication by mechanical, battery powered, electric, pneumatic, or any other means of force.

Figure 8:
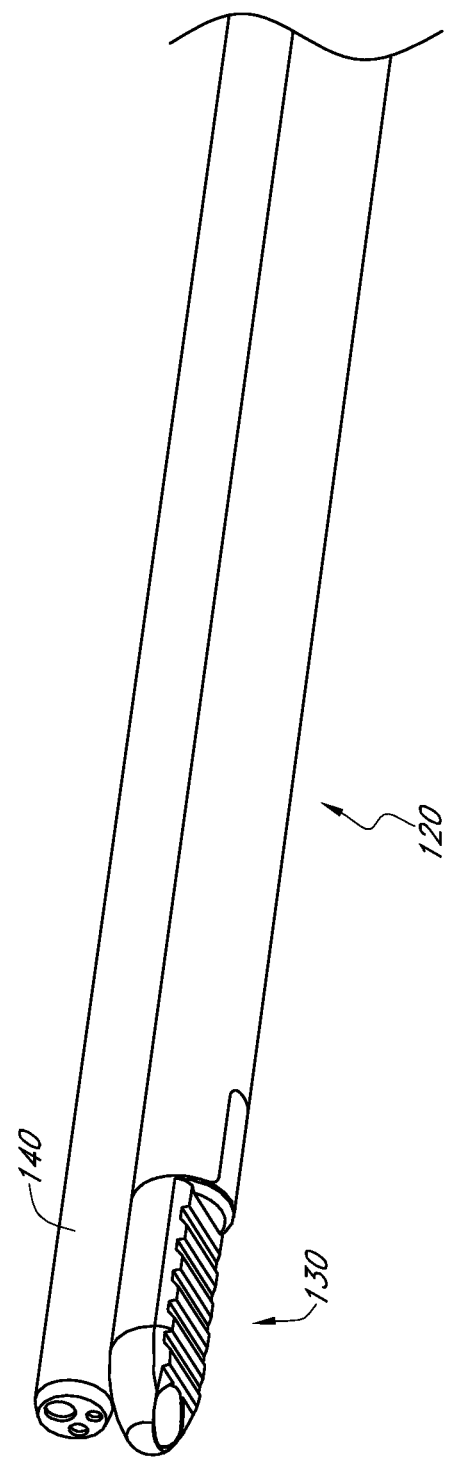
FIG. 8 illustrates a distal tip of an example embodiment of a bone graft delivery device including an endoscope.

The tip 130 may be made of a metallic, radiopaque material to facilitate visualization on, for example, fluoroscopy or x-ray. Alternatively, the tip 130 may be made of another material, for example a durable medical plastic or a composite material, and may include markers to facilitate visualization. In some embodiments, the bone graft delivery device 100 can include an endoscope or endoscopic camera to allow for visualization during insertion of the tip 130 to the target area, decortication, and/or delivery of the graft material. As shown in FIG. 8, an endoscope 140 can extend along the tube 120 and can be removably or permanently coupled to the tube 120.

In one embodiment, the device 100 described herein may be used in minimally invasive spinal surgery. For example, in a conventional posterolateral spine procedure, screws and or fusion cages may be delivered to adjacent vertebrae using small incisions made in a patient's back. It may additionally be desirable to deliver bone graft material to the surgical location, e.g., to the transverse processes, disc spaces, or facet joints, through one of these small incisions. The device described herein is sized to be delivered through a minimally invasive opening made in the patient's skin (e.g., through a skin incision of 4 cm or less), and configured so that the tip can be positioned adjacent a pedicle screw or other desired location. The curvature of the tube 120 can facilitate positioning of the tip 130 at desired spinal locations and allows, for example, insertion of the device 100 through an incision over one vertebra, and positioning of the tip 130 at an adjacent vertebra. Alternatively, the device can be delivered through any desired opening made in the patient's skin (e.g., minimally invasive or open). The jagged edges or other surface 134 on the device can be used to decorticate desired bone locations, causing bleeding of the bone and creating a surface that promotes bone fusion. The trigger 110 or other actuation mechanism can then be actuated to deliver bone graft material through the tube 120 lumen and openings 132 in the tip 130 to promote fusion of the bone.

Although use of the device 100 has been described with respect to an example spinal procedure, the device 100 can also be used in other spinal procedures and other orthopedic applications to deliver bone graft material to other locations in the body (for example, the femur or tibia).

Various modifications to the implementations described in this disclosure may be readily apparent to those skilled in the art, and the generic principles defined herein may be applied to other implementations without departing from the spirit or scope of this disclosure. Thus, the disclosure is not intended to be limited to the implementations shown herein, but is to be accorded the widest scope consistent with the principles and features disclosed herein. Certain embodiments of the invention are encompassed in the claim set listed below.

What is claimed is:

1. A bone graft delivery system, comprising:
   an elongate tube;
   a handle at a proximal end of the tube configured to be actuated to deliver bone graft material through the tube, the handle comprising:
      a funnel at a proximal end of the handle, the funnel configured to receive bone graft material;
      a channel extending between and in fluid communication with the funnel and the proximal end of the tube; and
      a ratcheting mechanism configured to advance bone graft material from the funnel, through the channel, and into the tube; and
   a plunger configured to be removably received in the channel and tube.

2. The bone graft delivery system of claim 1, wherein the ratcheting mechanism is configured to advance the plunger distally within the channel and tube to advance bone graft material distally through the tube.

3. The bone graft delivery system of claim 1, further comprising a distal tip at a distal end of the tube.

4. The bone graft delivery system of claim 3, wherein the distal tip is removably coupled to the distal end of the tube.

5. The bone graft delivery system of claim 3, wherein the distal tip is generally bullet shaped.

6. The bone graft delivery system of claim 3, wherein the distal tip is generally flat.

7. The bone graft delivery system of claim 3, wherein the distal tip comprises at least one rasping surface configured to decorticate bone.

8. The bone graft delivery system of claim 3, wherein the distal tip comprises at least one opening configured to deliver bone graft material.

9. The bone graft delivery system of claim 1, further comprising a shaft having a burr at a distal end, the shaft configured to be inserted through the tube and the burr configured to decorticate bone.

10. The bone graft delivery system of claim 1, wherein the tube is straight.

11. The bone graft delivery system of claim 1, wherein the tube is curved.

12. The bone graft delivery system of claim 1, further comprising an endoscopic camera positioned adjacent the tube.

13. A method for delivering bone graft material to a surgical location, comprising:
   providing a bone graft delivery device comprising an elongate tube and a handle at a proximal end of the tube, the handle comprising:
      a ratcheting mechanism;
      trigger operatively coupled to the ratcheting mechanism;
      a proximal opening; and
      a lumen extending between and in fluid communication with the proximal opening and the proximal end of the tube;
   loading bone graft material into the bone graft delivery device;
   positioning the device adjacent the surgical location;
   inserting a plunger into the lumen and tube;
   manipulating the trigger so that the ratcheting mechanism engages the plunger; and
   delivering bone graft material through the lumen of the handle and the tube by actuating the trigger to cause the ratcheting mechanism to distally advance the plunger.

14. The method of claim 13, wherein loading the bone graft material comprises loading the bone graft material into the proximal opening.

15. The method of claim 13, further comprising inserting a rasping instrument through the proximal opening and lumen of the handle and the tube and decorticating bone with the rasping instrument.

16. The method of claim 13, further comprising decorticating bone with a tip at a distal end of the tube, the tip having at least one opening for delivering the bone graft material to the surgical location.

17. A bone graft delivery system, comprising:
   an elongate tube;
   a handle at a proximal end of the tube configured to be actuated to deliver bone graft material through the tube, the handle comprising:
      a funnel at a proximal end of the handle, the funnel configured to receive bone graft material;
      a channel extending between and in fluid communication with the funnel and the proximal end of the tube;
      a ratcheting mechanism configured to advance bone graft material from the funnel, through the channel, and into the tube; and
      a trigger configured to be actuated to deliver the bone graft material through the tube.

* * * * *